United States Patent [19]

Gram

[11] Patent Number: 4,478,086

[45] Date of Patent: Oct. 23, 1984

[54] LOAD FRAME CROSSHEAD CONSTRUCTION

[75] Inventor: Martin M. Gram, St. Louis Park, Minn.

[73] Assignee: MTS Systems Corporation, Eden Prairie, Minn.

[21] Appl. No.: 456,504

[22] Filed: Jan. 7, 1983

[51] Int. Cl.³ .............................................. G01N 3/08
[52] U.S. Cl. ......................................... 73/781; 73/826
[58] Field of Search ................. 73/781, 782, 796, 798, 73/826, 828, 837

[56] References Cited

U.S. PATENT DOCUMENTS 3,714,821  2/1973  Gilley .................................... 73/781
4,235,114  11/1980  Mohler .................................. 73/826

OTHER PUBLICATIONS

MTS Systems Corporation Catalog, *MTS Interactive Material Test System Catalog*, No. 810.08-01, Jan., 1980.

*Primary Examiner*—Anthony V. Ciarlante
*Attorney, Agent, or Firm*—Kinney & Lange

[57] ABSTRACT

A material testing apparatus for testing physical properties of a test specimen includes an improved crosshead member adjustably supported on spaced vertical columns and adapted to support a grip for a test specimen to be loaded along a load axis. The improved crosshead member includes a load measuring (load cell) section defined by four spaced-apart openings located symmetrically with respect to the load axis. As shown there are two openings on each side of the load axis. The openings extend through the crosshead member. The crosshead is reduced in thickness or cross section between the openings to raise the stress levels in the crosshead so that strain gages are applied directly to the measuring section and can be used to measure the load applied to a test specimen. The grips are supported on a surface that is perpendicular to the loading axis and which intersects or is supported substantially on the point where there is substantially no lateral stress (in direction between the support columns) during either tension or compression loading of the specimen.

18 Claims, 10 Drawing Figures

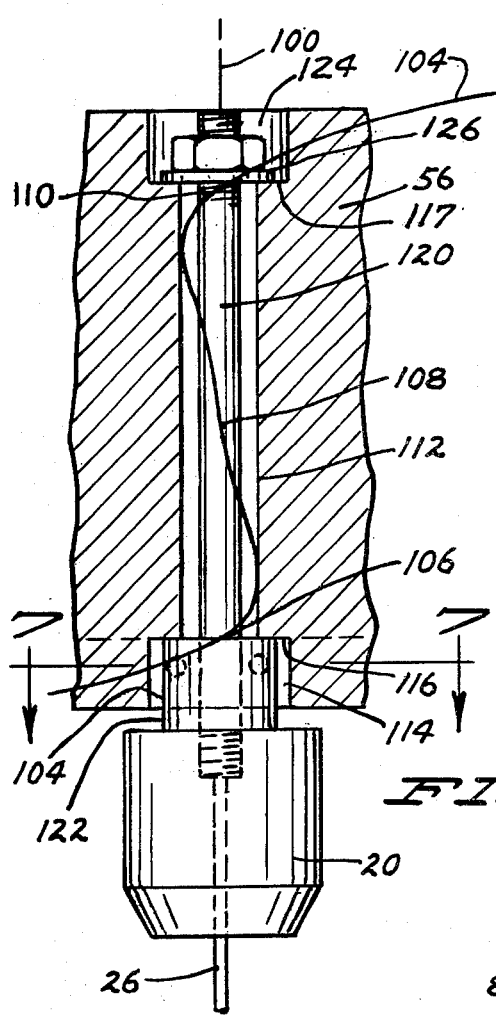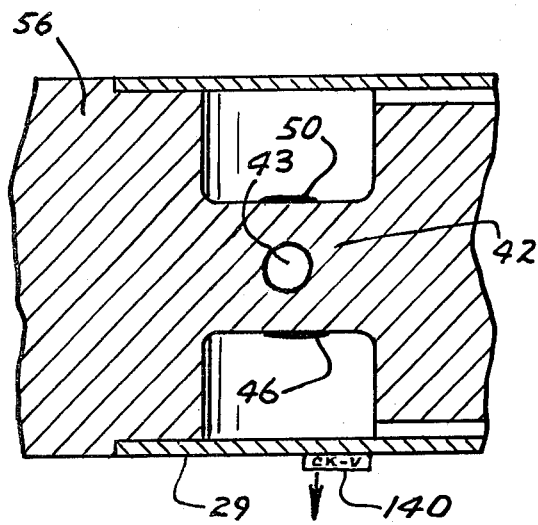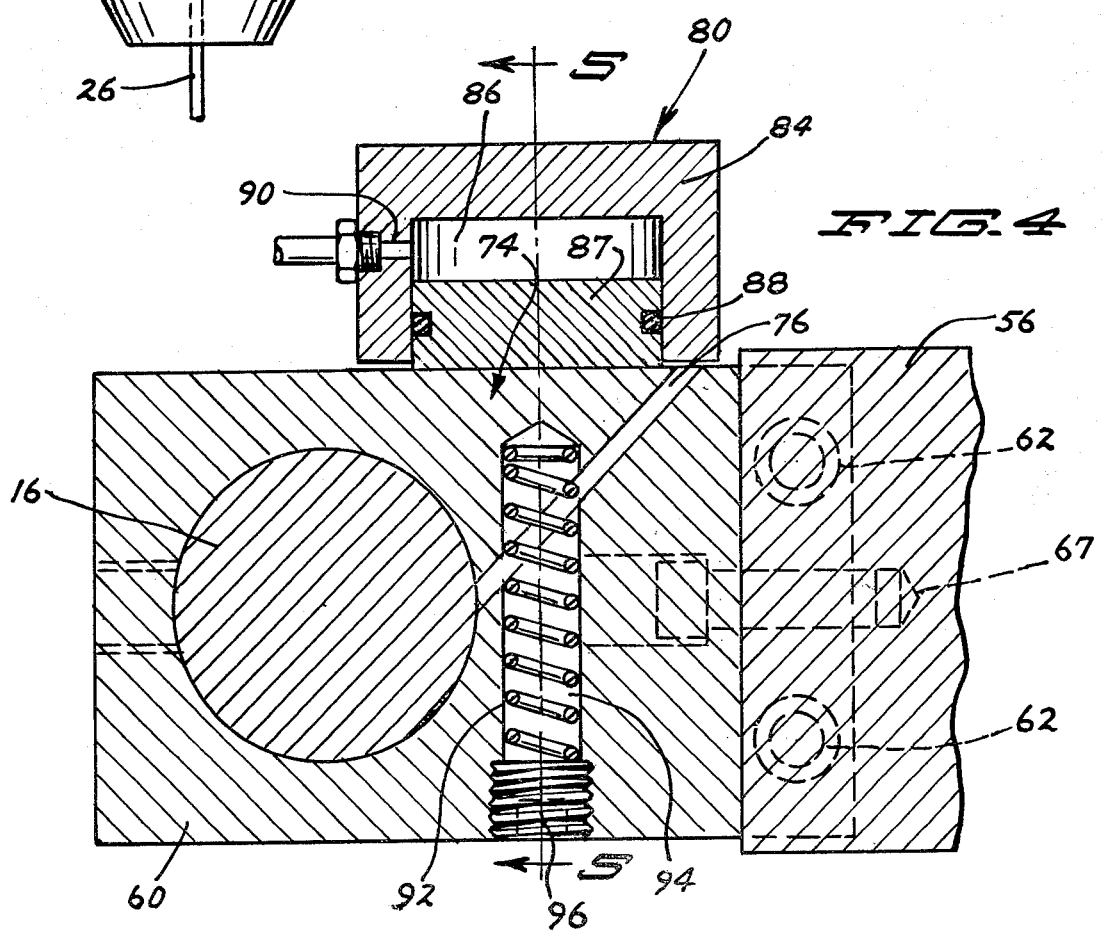

LOAD FRAME CROSSHEAD CONSTRUCTION

BACKGROUND OF THE INVENTION

1. Field of the Invention

The present invention relates to material testing apparatus for testing physical properties of test specimens, and in particular, it relates to testing apparatus wherein the loads applied to the testing specimens are measured in the crosshead member.

2. Description of the Prior Art

Material testing equipment is used to test the physical characteristics of materials such as metals or plastics. The materials are cut into test specimens according to established standard testing procedures. The test specimens are then placed in the load frame and are held by grips and tested under tension and/or compression loads. In the case of a test specimen tested under tension, data is obtained to develop relationship such as a stress/strain curve wherein physical properties such as elasticity, yield and fracture toughness, among others, are measured. Typical material testers are produced by MTS Systems Corporation of Minneapolis, Minn. and are illustrated in its catalog entitled, "MTS Interactive Material Test System Catalog." Although the typical test frame, such as is manufactured by MTS Systems Corporation, satisfactorily tests test specimens, there is a need for improving the accuracy of testing such test specimens, conserving space and reducing cost.

In the MTS test frames, but upper grip that holds the test specimen is a stationary grip and is attached to a crosshead member which is clamped onto supporting posts. The grip is attached to the crosshead through a load cell which measures load forces encountered during a testing cycle. The load cell takes up valuable vertical space between the crosshead and the upper grip, extending the height of the machine and limiting the amount of space for testing the test specimen.

In addition, the crosshead member needs to be attached to the upright supports of the testing machine such that it can be adjusted to accommodate specimens of various lengths and such that no movement of the crosshead member which could interfere with the load cell measurements occurs during a testing cycle. Hydraulically operated clamps presently are used on crosshead members. The crosshead may be held with other clamps or methods of securing the crossheads, such as threaded columns, shrink lock clamps, and nonadjustable or fixed crossheads may be used.

SUMMARY OF THE INVENTION

The present invention includes a crosshead for a testing machine or load frame which has a measuring section for measuring loads carried by the crosshead without a separate load cell. The measuring section is defined by spaced apart transverse openings extending through the crosshead member. The crosshead has reduced thickness webs in the measuring section on which strain gages are mounted.

When the crosshead is subjected to loads to load a specimen in both tension and compression there are tension and compression forces created along the upper and lower surfaces of the crosshead. However, there are points along the vertical, central axis of the crosshead where the lateral strains are substantially zero. These points are spaced from the upper and lower edges of the crosshead, and will be called the point of zero lateral strain.

In the present device the upper specimen grip is mounted on a plane surface lying substantially on the lower point of zero lateral strain. The upper grip is thus supported on the crosshead member at a location which reduces tendency of the grip to fret or slip slightly due to differential strain between the end surface of the grip and the supporting surface of the crosshead during a testing cycle.

The measuring section includes at least two webs forming measuring areas, each measuring area having a cross section small enough to reach a strain level easily detected by strain gages to provide for measurement of forces applied to the test specimen. As shown, each measuring area extends vertically between an upper and a lower transverse opening.

The crosshead member is clamped at each end to an upright column, as shown by use of a bore having an inner surface that circumferentially surrounds each upright column. A clamping slot extending along the length of each bore and vertically through the crosshead member. The slot defines a flexing clamp section mounted on the end crosshead member which may be clamped by a suitable clamping mechanism such as a hydraulically actuated piston, so that the inner surface of the clamping bore grips tightly around the respective upright column and clamps the crosshead member securely to each upright column. In one embodiment the slot forms an acute angle with respect to the plane of the crosshead, and opens toward the inside of the respective column rather than to the outside of the column as is normally done.

BRIEF DESCRIPTION OF THE DRAWINGS

FIG. 3 is a fragmentary cross sectional view of the measuring areas on which load measurements are taken, the cross section being taken along the line 3—3 in FIG. 2;

FIG. 4 is a fragmentary sectional view of a clamping mechanism taken along line 4—4 in FIG. 2;

FIG. 6 is a fragmentary cross sectional view of the upper grip mounting arrangement taken along the line 6—6 in FIG. 1;

DETAILED DESCRIPTION OF THE PREFERRED EMBODIMENTS

Figure 1:
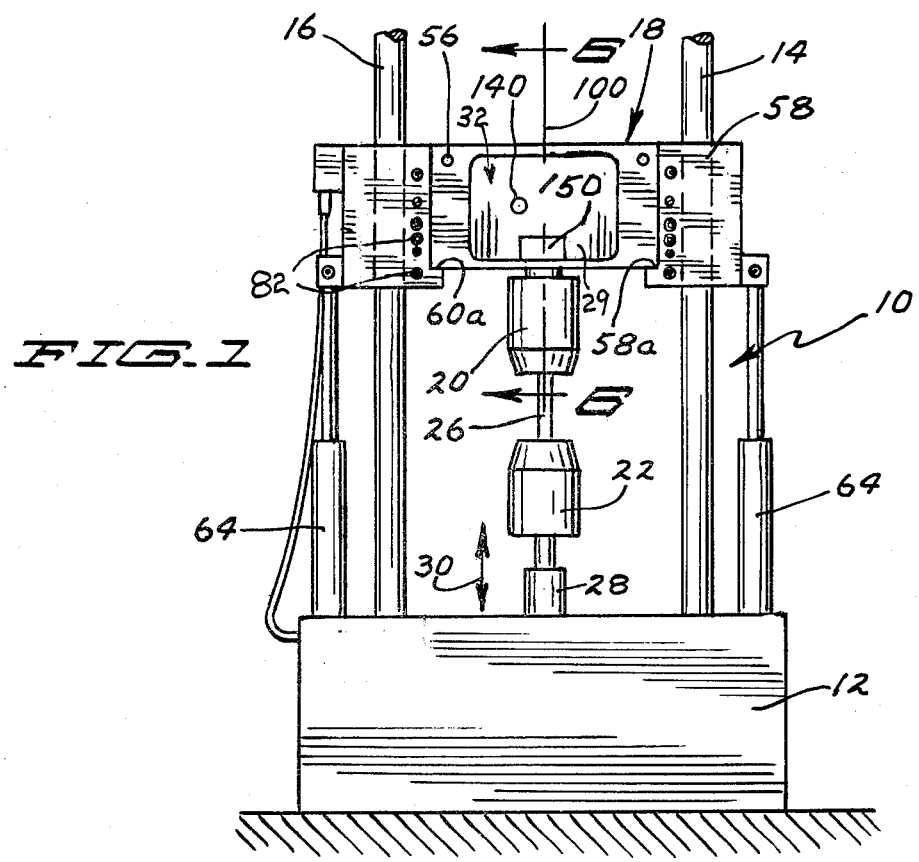
FIG. 1 is a partial elevational view of a material tester showing the improvement of the present invention.

A mechanical test machine or load frame is generally illustrated at 10 in FIG. 1. The frame 10 includes a base 12, a pair of upwardly extending support columns 14 and 16, and a crosshead 18. An upper grip 20 is supported on the crosshead 18 and a lower grip 22 is connected to the rod of a hydraulic actuator 28 which loads a test specimen 26 held in the grips. The loading is in opposite directions indicated by arrow 30 and under control of a servovalve in a normal manner. A cover plate 29 covers a load cell or load measurement section 32 which is used for measuring the test loads, and this eliminates the need for a separate load cell in the specimen support section.

Figure 2:
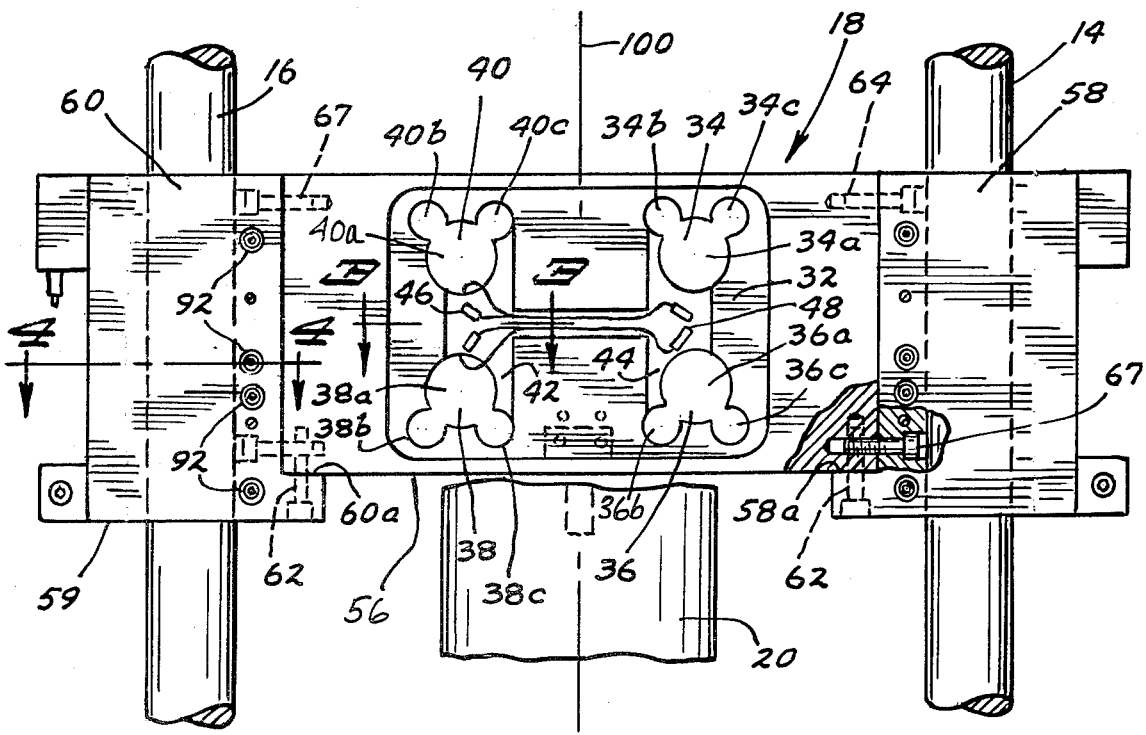
FIG. 2 is an enlarged fragmentary elevational view of the crosshead member of the present invention.

FIG. 2 shows an enlarged elevational view of the crosshead 18 of the present invention. The crosshead 18 reacts load forces that are applied to the test specimen by actuator 28. The crosshead member 18 includes the measurement section 32 to measure loads on the test specimen.

The measurement section 32 is defined by sections of reduced cross sectional areas in the crosshead member. The reduced cross section areas raises the strain in such areas to a level that can be reliably measured with strain gages. The measurement section 32 is defined by four openings 34, 36, 38 and 40 extending through the crosshead member and spaced from each other in a quadrilateral arrangement. The opening 34 is preferably directly above opening 36 and the opening 40 is directly above opening 38. The openings 34, 36, 38 and 40 are symmetrically located with respect to the axis of loading of the specimen which is indicated at 100. Each opening 34, 36, 38 and 40 contains a primary bore, as noted in opening 34 as 34a, and two secondary bores, as noted in opening 34 as 34b and 34c. The secondary bores 34b and 34c are spaced from each other and intersect the primary bore 34a. The other openings 36, 38 and 40 contain similarly arranged primary bores 36a, 38a and 40a and secondary bores 36b, 36c, 38b, 38c, 40b and 40c, respectively, as illustrated in FIG. 2.

In addition to the openings 34, 36, 38 and 40, the measurement section 32 also includes measurement webs 42 and 44 having a reduced thickness to raise the strain under normal loading on the crosshead to a level where the strain can be accurately measured. The reduced thickness is illustrated in FIG. 3. FIG. 3 is a fragmentary cross-sectional view taken along the line 3—3 of FIG. 2 and shows the web 42 which extends between the openings 40 and 38. Similarly, web 44 lies vertically between the openings 34 and 36. As should be noted from FIG. 3, the webs or reduced areas 42 and 44 are preferably reduced in thickness equally from both the front and rear side surfaces of the crosshead member 18, and thus are symmetrical in relation to the bisecting plane of the crosshead 18 which passes through the axes of columns 14 and 16. A hole 43 can be drilled vertically through each web to further increase the strain under loads in the immediate location of the strain gages.

Figure 8:
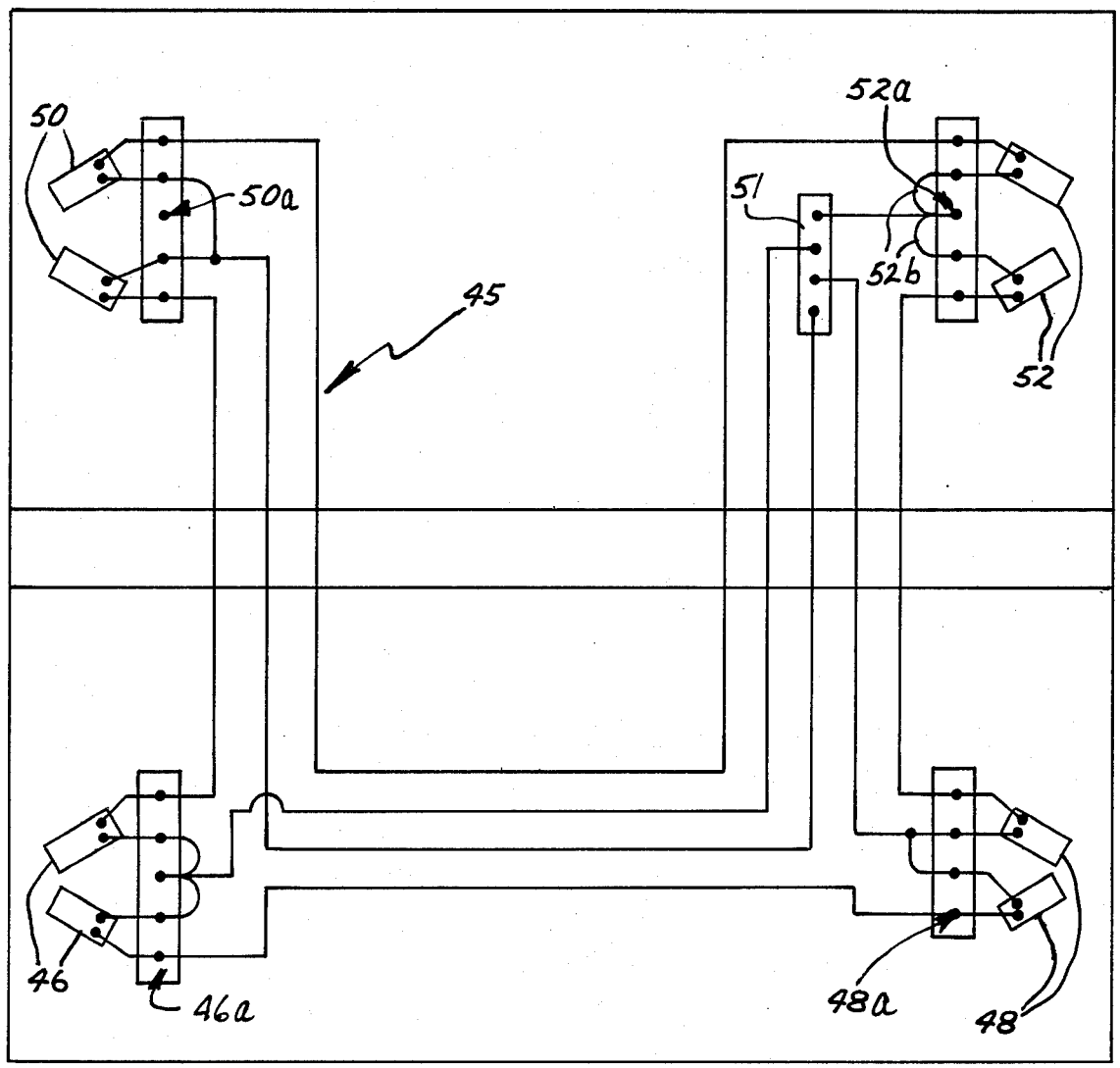
FIG. 8 is a schematic view of the strain gage bridge used in the present invention showing the opposite sides of the crosshead folded outwardly in flat layout.

A strain gage bridge 45 includes a plurality of pairs of strain gages 46, 48, 50 and 52 which are positioned on the side surfaces of the measurement webs 42 and 44. As illustrated in FIGS. 2 and 8, a pair of strain gages 46 are placed on one side surface of the measurement web 42 and the strain gages 50 are placed on a side surface opposite from the strain gages 46. The strain gages 48 and 52 are similarly positioned on the measurement web 44.

The arrangement of the strain gage bridge 45 is illustrated in FIG. 8. The strain gage bridge 45 is a typical type of strain gage bridge having strain gages of the resistance type. The bridge arrangement, as illustrated in FIG. 8, detects strain in the measurement webs 42 and 44 and provides a suitable signal for monitoring and recording loads applied to the test specimen 26. Normally, a separate load cell is provided in series with at least one of the grips between the base and crosshead and the present arrangement eliminates such need. The instrumentation or readout equipment is well known. The gages are bonded to the surfaces of the webs 42 and 44 in a normal manner and are coupled to connecting blocks 46a, 48a, 50a and 52a. The blocks 46a, 48a, 50a and 52a have terminals which permit connection for separate resistors for trimming the resistances for bridge balance. Further block 51 provides terminals for shunting the bridge legs for balance.

In addition, the terminals of the blocks 46a and 52a are used for connecting temperature compensation resistance wires shown at 46a and 52a. The amount of temperature compensation can be selected as desired.

The purpose of the cutouts in the crosshead is to separate some of the load or stress components from the sensitive strain gage area which comprises the shear beam or web area 42 and 44. The crosshead is symmetrical and on one side, bores 34a and 36a define the shear beam or web 44 on which the strain gages are mounted. On the left-hand side bores 38a and 40a define the shear beam or web 42. The bores 34b, 34c, 36b and 36c and bores 40b, 40c, 38b and 38c, along with the top and bottom edge of the crosshead define four flexural pivots on each side of the loading axis. The effect is top and bottom links to the center of the crosshead that are "soft" in vertical deflection and stiff axially (horizontally). The flexures therefore carry the major part of the bending moment but only a minor portion of the shear force which is imposed by a vertical load applied at the center of the crosshead.

Since the center shear beam or webs 42 are additionally reduced in cross section, the flexural pivots are also stiffer than the webs with respect to torsional moments, side loads, and bending moments imposed at the center, and therefore tend to isolate the shear beams or webs 42 from those extraneous loads.

Strain gages are mounted to the shear beams or webs in the direction sensitive to shear stesses. The shear beam approach eliminates the inherent adiabatic heating and cooling that causes transient errors in bending beam and column cells. The eight strain gages are wired in a bridge circuit so that most extraneous stresses tend to cancel.

The design of the load transducer elements as described above utilizes principles that are commonly practiced in transducer manufacture.

Figure 10:
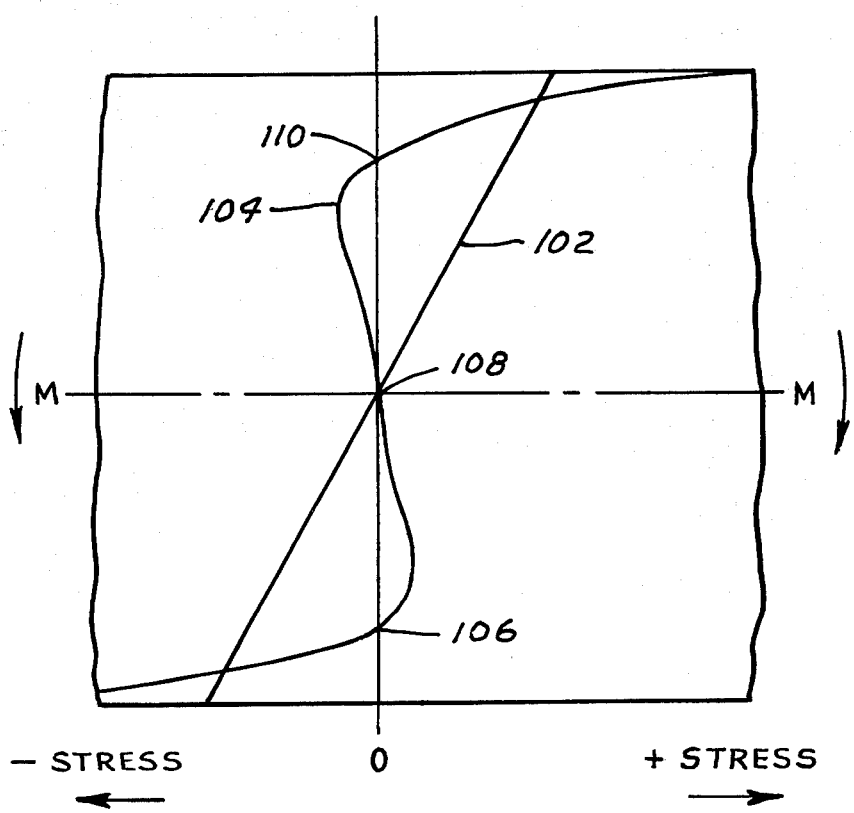
FIG. 10 is an enlarged schematic representation showing transverse stress distribution of the crosshead of the present invention.

A second result of locating the flexural pivots to carry most of the bending stress at the location of the load sensor is that it tends to change the stress pattern in the center section of the crosshead. In a rectangular cross section beam, the stress due to a moment at any point in the beam is given in strength of materials text books as $$S = M X / I$$

where
M is the moment
I is the moment of inertia
X is the distance from the neutral axis or centerline
FIG. 10, in curve or line 102, shows the text book stress distribution in such a normal beam. Curve 104 in FIG. 10 and also in FIG. 6, approximates the stress distribution in the center section of the present crosshead resulting from locating the cutouts or bores on either side of it. The stress is concentrated at the upper and lower surfaces and actually shows a stress reversal at three points instead of the one point predicted by the text book formula.

Grips are mounted to the center of the crosshead as mentioned. A common method used to mount grips on conventional crosshead is through a load cell that has a surface of the cell (or grip) against the bottom surface of the crosshead and fastened tightly using a stud vertically through the crosshead.

As load is applied, from curve 102 it can be seen that the surface of the crosshead expands or contracts laterally and the contacting surface of the grip or load cell does not, resulting in slippage between the surfaces. The resulting frictional loads on the surfaces mating or contacting cause a small but measurable change in stress pattern in the cell and would result in hysteresis.

The crosshead 18 is made up in individual sections including the center section 56, which includes the webs and the openings as previously described. In the first embodiment of the invention this center section 56 is held in a pair of clamp sections 58 and 60, respectively, which are identical except that they are for right and left hand operation. The clamp sections 58 and 60 are provided with lower shoulder surface shown at 58a and 60a which engage and support the center section 56. The center section is actually bolted to the clamp sections 58 and 60. For example, lower cap screws indicated at 62 extend from through the shoulder surfaces 58a and 60a and are threaded into the center section 56. Additional cap screws 67 that extend laterally through portions of the clamp sections are threaded into the center section in generally horizontal direction. These cap screws 67, for example shown in FIGS. 2 and 4 have their heads recessed so that their heads are adjacent to the edges of the center section 56, and thread into the ends of the center section 56 to hold the crosshead sections securely in an assembly.

The clamp sections 58 and 60 are used for supporting the crosshead with respect to the columns 14 and 16, respectively. The clamp is a hydraulically operated clamp using a slit that provides a split-type clamp. The crosshead assembly 18 is raised and lowered through the use of hydraulic cylinders shown only schematically at 64 on opposite sides of the crosshead, and acting between the base 12 and the crosshead 18 to permit raising and lowering the crosshead 18 to a desired level. Then, when the crosshead is in working position, the clamps on the clamp sections 58 and 60 are actuated to hold the crosshead securely on the columns.

Figure 5:
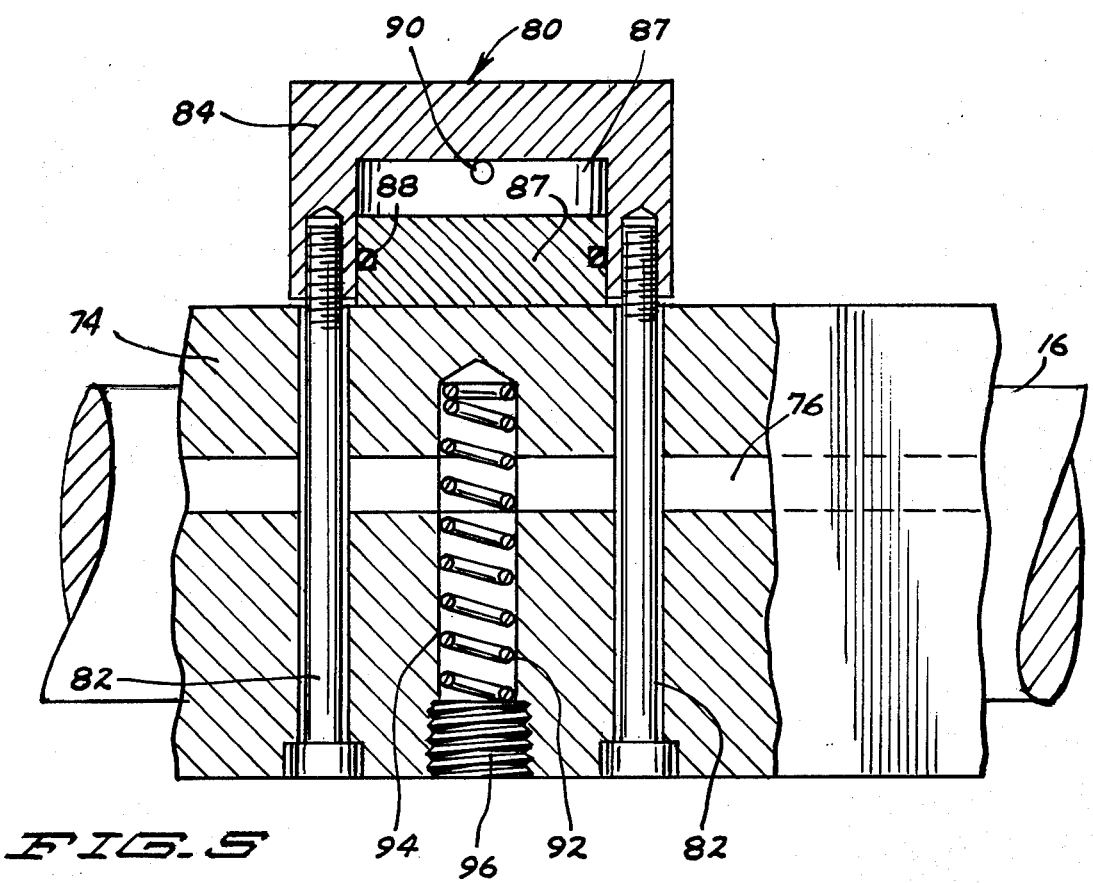
FIG. 5 is a fragmentary sectional view taken along line 5—5 in FIG. 4.

Referring to FIGS. 4 and 5, a typical actuator of each of the clamping sections 58 and 60 is shown. The clamping section 60 is illustrated, but the locking is exemplified for both of the clamping sections. Each of the clamping sections has a bore to slidably receive the column 14 and 16. Column 16 is shown in FIGS. 4 and 5. The clamp block 60 has typically a diagonal slot 76 which extends vertically through the entire clamping section and which opens to the exterior on the rear side of the crosshead 18 as shown. It provides for the ability to flex portions of the clamping section 60 relative to the column 16 (or 14) by having reduced section areas on three sides of the column itself. The flexing member shown at 74 tends to bend in three areas around the respective column where the cross section is the smallest, thus tending to aid in equalizing the clamping stresses and loads onto the column itself.

As shown, the slot 76 forms an acute angle with respect to the bisecting plane of the crosshead. The clamping of each of the clamping sections is accomplished with two vertically spaced hydraulic cylinder assemblies, one being illustrated generally at 80. These cylinder assemblies are each held relative to the respective clamping sections 58 and 60 with a pair of cap screws 82 (FIG. 5) which extend through provided bores in the clamping section, as shown in clamping section 60, and are threaded into a hydraulic cylinder block 84. The heads of the cap screws 82 are recessed in provided openings. As can be seen, the cap screws 82 extend across the slot 74 (see FIG. 5 in particular). The cylinder member 84 has an interior cavity 86 which houses a piston 87. The piston is movable in the cavity 86, and has an O-ring seal 88 that seals an upward chamber portion shown in FIG. 5 so that fluid under pressure introduced into this chamber from a pressure inlet 90 causes the piston 87 to be pushed against the backside surface of the clamping section, that is onto the flexing portion 74, and the force is reacted through the cap screws 82 to the opposite side of the clamping section, which therefore tends to reduce the size of the slot 76 and clamp the column 14 or 16 tightly.

All of the hydraulic actuator assemblies 80 operate in this manner, and tightly grip the column at two vertically spaced places of each of the clamping members 58 and 60. Two such assemblies 80 are vertically spaced on each clamping member.

Once the hydraulic pressure is released from chamber 86, a spring 92 is provided inside a bore 94 that is extended through the clamp assemblies and deadends in the flexing or clamping section 74, as shown in FIG. 5, to provide a spring force tending to open up the slot 76 at all times. A set screw 96 may be used for holding the spring 92 in place and also to provide some adjustment of the spring force if desired. Several springs 92 can be used if desired.

As can be seen in FIG. 5, and also in FIG. 4, cap screws 64, which are the horizontal cap screw, extend through the clamp sections, and through provided bores therein. These bores in the clamping sections for the cap screws 64 are drilled from the outside surface of each of the clamping sections through the bores for the respective column 14 and 16. The heads of the cap screws 62 will be supported adjacent to the junction line between the center block portion 56 and the respective clamping sections 58 and 60. The number of cap screws 64 that are used can be varied as desired.

The hydraulic pressure that is provided in the chamber 86 to act in the piston 87 may be varied to suit existing circumstances and provide the necessary clamping for reacting the loads exerted on the test specimen.

As shown in FIGS. 6 and 10, the loading axis 100 of the specimen bisects the crosshead. A plane perpendicular to the central plane of the crosshead 18 (between the columns) and passing through the loading axis 100 defines a central loading plane. The webs or shear beams 42 and 44, and openings 34, 36, 38 and 40 are located symmetrically with respect to such loading plane. The specimen is loaded in both tension and compression and thus the lower edge of the crosshead 18 will also carry both tension and compression stress during a loading cycle.

Also illustrated in FIGS. 6 and 10, as briefly explained, are a theoretical rectangular beam stress curve 102 and an approximation of the lateral stress curve of the present crosshead (curve 104) which illustrates the lateral stress present along the vertical height of the crosshead 18 at the central axis 100 during tension loading of a specimen (curve 104). Curve 102 (standard crosshead) goes to zero stress where it crosses the axis 100. There is no internal strain in a lateral direction parallel to plane of the crosshead where either the curve 102 or 104 cross the axis 100.

As shown by curve 104 there are three points of zero strain and one such point is close to the lower edge of the crosshead. The curve 104 illustrates that there are points along the axis 100 where lateral strain is at a minimum or during loading of the specimen. A more reliable, lower hysteresis mounting for the upper specimen grip can be provided with the present crosshead.

A plane perpendicular to the loading axis 100 and passing through the lower zero stress point is used to support the upper grip 20 relative to the crosshead 18 to minimize the tendency of the upper grip to creep on its supporting surface. Such zero lateral strain points are shown at 106, 108 and 110 in FIGS. 6 and 10.

As stated, the openings 34, 36, 38 and 40 and the measurement webs 42 and 44 are positioned symmetrically on opposite sides of a center plane perpendicular to the plane of the crosshead member 18. A bore 112 extends vertically through the central section 56 of the crosshead 18, and is substantially concentric with the loading axis 100. A counterbore 114 is machined into the lower portion of the center section of the crosshead 18 concentric with the bore 112, and the counterbore 114 has a planar inner surface 116 lying perpendicular to the axis 100 and lying on the lower zero lateral strain point represented at 106. This surface 116 thus defines a plane where substantially zero lateral strain is present in the crosshead. Again, the curve 104 is to be considered illustrative rather than precise as in an actual measurement. Also the upper edge of the crosshead is counter bored as at 124 to provide a surface 117 substantially lying on the point of zero lateral strain 110 near the top edge of the crosshead. Surface 117 is also perpendicular to axis 100.

The upper grip 20 is attached to a bolt 120 threaded into the upper end of the grip. The bolt 120 extends upwardly through a support sleeve 122 and then through the bore 112 to the upper side of the crosshead 18. The upper counterbore 124 receives a washer 126 that rests against the inner end surface 117 of the counterbore 124. A nut 126 engages the external threads of the bolt 120 and may be tightened onto the washer 126 to in turn clamp the grip and the support sleeve 122 tightly against the surface with the support being reacted to surface 117. The surface 116 and 117 as stated define planes where there are substantially no lateral strain in the crosshead. The junction surface, therefore, between the support sleeve 122 and the surface 116 forms the loading junction surface between the crosshead and the specimen. The surface 117 reacts the load from bolt 120 and also is a surface of substantially no lateral strain.

The upper load carrying grip 20 is therefore held along a surface where there is no substantial tendencies for the grip to slip because of relative movement in between the surfaces where the grip is supported. This results in reducing the component of hysteresis due to grip mounting by more than an order of magnitude. The mounting nut used for mounting the grip must be similarly recessed.

Figure 7:
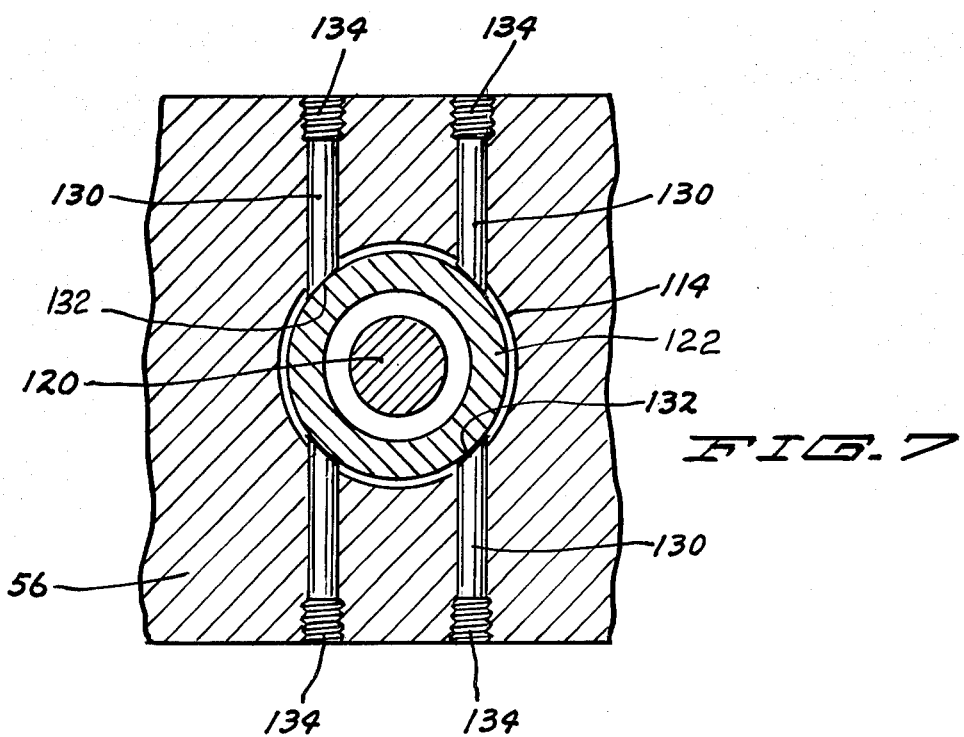
FIG. 7 is a sectional view taken along line 7—7 in FIG. 6.

In FIG. 7, the center section 56 of the crosshead member 18 is shown in cross section, to illustrate a method of adjusting the support sleeve 122. As can be seen, the bore 114 is of larger diameter than the outer diameter of the tube 122, and also it can be seen that the bolt 120 is positioned within the sleeve 122. The sleeve 122 and grip 20 are piloted together so that they move laterally as a unit.

To locate the sleeve 122 so that the position of the grip 20 can be adjusted to be substantially concentric with the lower grip 22, a plurality of fore and aft extending bores are provided in the center portion 56 of the crosshead. Each of the bores has a dowel 130 slidably mounted therein, and the ends of the dowels are beveled so that they will engage the outer side surfaces of the sleeve 22. These end surfaces indicated at 132 are tapered at approximately 45° to the longitudinal axis of the dowels. The dowels are pressed against the tubes 122 to provide for precise location, and the adjustments are through the use of set screws 134 that are threadably mounted in the provided bores for the dowels at the outer ends and which can be adjusted so that the sleeve 122 can be slid transversely to the counterbore 114 until it is properly located. The central axis of the sleeve 122 should coincide with the loading axis 100. By using the four dowels 130 located on a same plane so they engage the sleeve 122, the axis of the sleeve 122 and this grip 20 can be shifted as desired.

As shown in FIGS. 1 and 3, the cover plates 29 will be used to seal the interior working of the strain gages and the like, and may be provided with a one-way check valve shown at 140 in FIG. 3, to permit air to bleed out, but not permit reverse flow to the interior. This one-way check valve thus prevents pressure from building up on the inside of the measuring section, but also insures that moisture laden air and the like does not enter the measuring section and cause corrosion or rusting.

Fatigue tests can be performed on the testing machines. With a large servo valve on the testing actuator, the tests may be performed at very high frequencies. At high frequencies, the mass of the grip and part of the load transducer mass times the acceleration can cause a significant error between the load on the specimen and the load measured by the transducer (at all frequencies an error exists but at lower frequencies—below 30 Hz for example—the magnitude is generally insignificant). One method to compensate for acceleration is to measure the acceleration of the masses and to sum that signal (with proper scaling) with the load signal. On a conventional system, it is difficult to mount an accelerometer because the need for a stiff (high resonant frequency) mounting generally results in the need to add length to the load cell.

In calculating precise loads that are generated during testing, the amount of acceleration of the crosshead can adversely affect the readings. In the present device, an accelerometer indicated generally at 150 (FIG. 1) may be fixed to the crosshead 18 adjacent the lower center sections thereof, to provide a reading of the acceleration on the crosshead and thus provide a compensation signal for use in calculating actual loads applied to the specimen and taking into account the accelerations that are present.

In the present device, the provision made for mounting the accelerometer to one side of the center section of the crosshead allows an undistorted acceleration measurement since a large high resonant frequency mounting can be provided. It does not interfere with the test space or add additional length requirements.

The overall assembly permits accurate loading, little creep of the grip and rapid, efficient clamping. Also the use of the accelerometer aids in accurate compensation.

Figure 9:
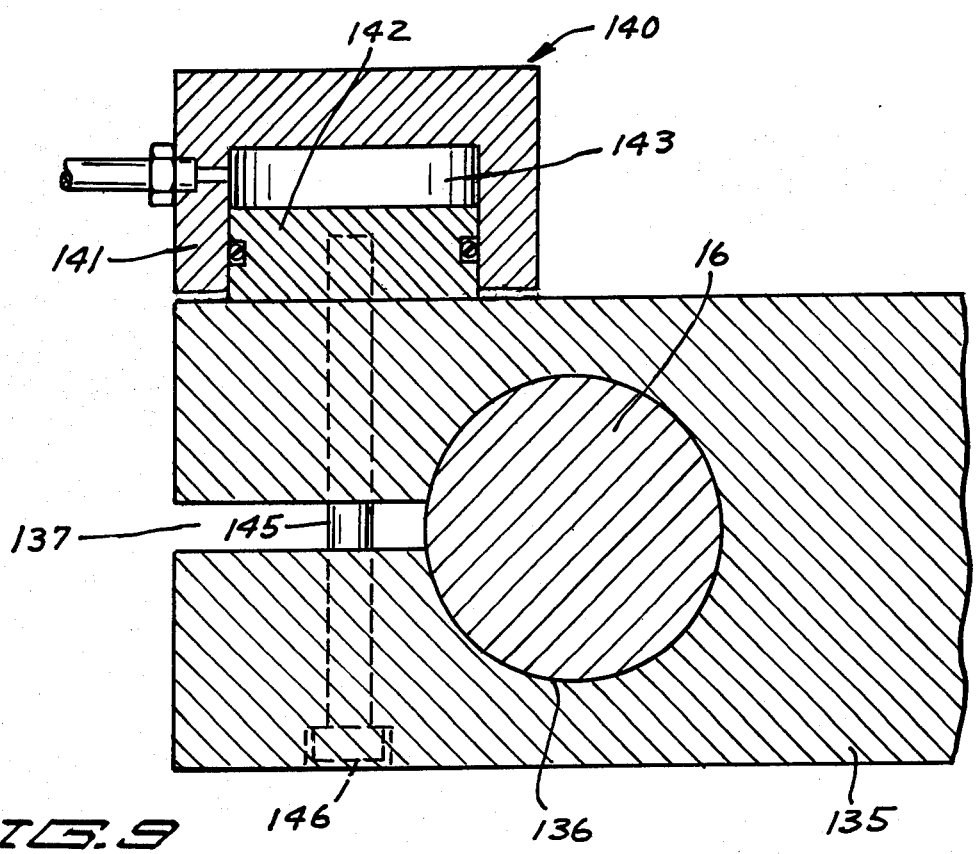
FIG. 9 is a part schematic cross sectional view of a further preferred embodiment of a clamp arrangement for the crosshead of the present invention.

With reference to FIG. 9, a further preferred embodiment shows a conventional arrangement for clamping the crosshead onto the vertical columns. In this embodiment, the crosshead is formed from a single or unitary piece of material that extends all the way across between the columns, and is not made in sections that are bolted together as in the first form of the invention. This further preferred embodiment is close to conventional crosshead construction insofar as the clamping is concerned, and shows that various methods presently known for clamping crossheads onto columns can be utilized with the crosshead of the present invention. The through bores providing shear carrying webs on which strain gages can be mounted are used, and the grip will be mounted on a surface where there is substantially zero lateral strain.

The crosshead shown at 135 is a unitary block of material that has the through bores on opposite sides of the loading axis 100 as with the previous form of the invention. Further as shown the block has a bore 136 for receiving a column such as column 16, and a slot 137 is formed at the outer edges of the crosshead 135 to form a pair of split type clamps (one for each column). A hydraulic cylinder arrangement for clamping the crosshead which operates in the same manner as the hydraulic cylinders 80 is shown at 140, and includes a cylinder housing 141, and an internal piston 142 mounted in an interior chamber 143. The piston 142 is sealed with respect to the chamber 143. The cylinder housing 141 is held by a bolt or cap screw 145 which extends from the opposite side of the crosshead, as shown at 146, across the slot 137 and which is threaded into the cylinder housing 141 in the same manner as the attachment of the cap screws 82 to the cylinder member 84 shown in FIG. 5.

Two cap screws 145 are used, but only one is shown for illustrative purposes. When fluid under pressure is introduced into chamber 143 above the piston, the hydraulic pressure will act through the hydraulic cylinder body 141, and cap screws 145 to react the forces to tend to close the slot 137 and clamp onto the column 16 in the same manner.

Thus this form of the invention is merely relating to the clamping means which can be incorporated into a unitary crosshead assembly rather than the multiple part crosshead assembly shown in the first embodiment of the invention. Further, the slit or slot for the hydraulic clamps can be a radial slot as shown, or a slot that extends at an acute angle with respect to the central plane of the crosshead if desired.

What is claimed is:

1. A load frame crosshead member for use with a load frame including a base, at least two upright support columns extending from the base for supporting the crosshead member and first and second means for retaining a test specimen between the crosshead member and such base during a testing cycle along a generally centered loading axis parallel to the upright supports, the improvement comprising:

a measuring section in the crosshead member defined by a plurality of spaced apart openings extending through the crosshead member and arranged laterally symmetrically relative to the loading axis, the openings on each lateral side of the loading axis comprising two openings vertically spaced and formed by a web section formed sufficiently thin to be stressed to a measurable level when a test specimen held in the load frame is loaded;

means for measuring stress positioned on the measuring webs; and clamping means located at each end of the crosshead member for clamping the crosshead to the upright supports.

2. The apparatus of claim 1 wherein said clamping means includes a clamping bore surrounding each upright support column and a clamping slot extending along the length of each bore and to an outside surface of the crosshead member, said slots defining planes relative to the plane of the crosshead member to define a flexing portion and means for flexing each flexing portion such that the inner surface of each clamping bore may be tightened around the respective upright column.

3. The improvement of claim 2 wherein the means for flexing comprises a hydraulic cylinder positioned on a first side surface of said crosshead, said side surfaces being generally parallel to the plane defined by the axes of the upright columns and bisecting the crosshead, bolt means to fasten said hydraulic cylinder relative to said first surface, said bolt means passing through provided passageways extending across the width of said crosshead member and spanning the respective slot, said bolt means having heads that react against the side surface of said crosshead opposite from the surface on which the hydraulic cylinder rests, a piston sealably mounted in said cylinder and resting against the first surface of said crosshead member, said piston defining a chamber on a side thereof opposite from the side of the piston engaging said first surface whereby when fluid under pressure is introduced into said chamber, said piston bears against the first surface and the heads of said bolts react force back to said second surface of said crosshead member from said hydraulic cylinder to thereby tend to narrow the width of the slot and cause the clamping action.

4. The improvement of claim 3 and spring means reacting on the portions of said clamping means on opposite sides of said slot whereby the spring means tend to urge said slot to open.

5. The improvement of claim 4 wherein said clamping means comprises another bore extending laterally in direction from one side surface of said crosshead member, spanning said slot and ending within the crosshead member, said spring means being mounted in said another bore, and having surfaces to react against, to tend to open said slot.

6. The improvement of claim 1 including accelerometer means mounted on said crosshead member, said accelerometer means being adapted to provide a signal indicating acceleration on said crosshead member during testing of a test specimen held by said crosshead member.

7. The improvement of claim 1 wherein said clamping means comprise separate sections and said measuring section comprises a separately formed section, and means to hold said clamping means at opposite ends of said measuring section to form a crosshead assembly.

8. The apparatus as specified in claim 7 wherein said means to hold comprise cap screws extending laterally from bores defined in said clamping means and threadably engaging the measuring section to hold the clamping means and the measuring section together.

9. The improvement of claim 1 wherein said clamping means comprise blocks having a bore defined therein, and said blocks having means forming a shoulder at the lower edges thereof, said measuring section mounting on the respective shoulders of each of said clamping means, said shoulders facing upwardly when the crosshead is installed on said support columns, and cap screw means urging portions of said measuring section against said shoulders to react vertical forces.

10. The apparatus as specified in claim 1 and cover members on opposite sides of said crosshead member to enclose and seal the openings through said crosshead member, and one-way check valve means mounted in at least one of said covers to permit air inside said openings to bleed outwardly, but to resist air from moving inwardly toward said openings through said cover member.

11. The improvement of claim 1 and including means to support the upper grip on relative to the measuring section, said means comprising a recess in the lower portions of said measuring section and generally centered on said loading axis and having an internal end surface generally perpendicular to said loading axis, said end surface defining a plane lying generally along a region of minimum strain in said measuring section in directions along the plane of said crosshead member between the upright support columns, and support means having a support surface that mates on said first-mentioned end surface, means to clamp said end surface and support surface together under a clamping load sufficient to carry the loads applied to the specimen, so the tendency of the interface between the end surface and support surface to fret is minimized.

12. The improvement of claim 1 wherein the means for measuring is a strain gage bridge including at least four strain gages, with at least one strain gage attached to each surface of the measuring webs.

13. The improvement of claim 2 wherein the means for flexing includes a flexing bore extending perpendicularly to a vertical plane of the crosshead member and through the clamping slot, and a fastener member fixedly supported on the crosshead member at a first end and extending through the clamping bore and clamping slot and having a second end, and force means for engaging the second end of the fastener member and flexing the flexing portion until the inner surface of the clamping bore is in clamping engagement with the upright column.

14. The improvement of claim 13 wherein the force means includes a hydraulically actuated piston fixedly attached to the second end of the fastener member.

15. The improvement of claim 2 and further including release means for flexing the flexing portion in a direction such that the inner surface of the clamping bore returns to an unclamping position.

16. The improvement of claim 15 wherein the release means includes a spring in compression within a bore in the crosshead and extending through the clamping slot, and means for holding the spring in compression.

17. In a load frame and crosshead member for testing specimen with a load force including a base, means supporting the crosshead member on the base at outer edge portion of the crosshead, and first and second grips for retaining a test specimen between the crosshead member and the base during a testing cycle along a generally centered loading axis, the improvement comprising:

a plurality of spaced apart openings extending through the crosshead member and arranged laterally symmetrically relative to the loading axis to provide a center section that is connected to the respective edge portions of the crosshead through flexure links that permit deflection of the center section in directions along the loading axis and are stiff in directions perpendicular to the loading axis, and through a respective web between the respective flexure links on each side of the loading axis to carry the major portion of the shear loads between the loading axis and the edge portions; and means to support the first grip relative to the center section of the crosshead comprising a recess in the lower portions of said center section and generally centered on said loading axis and having an internal end surface generally perpendicular to said loading axis, said end surface defining a plane lying generally along a region of minimum strain in said center section in directions between the edge portion for the grip having a support surface that mates on said first-mentioned end surface, means to clamp said first grip so said end surface and support surface are freed under a clamping load sufficient to carry the loads applied to the specimen through the grips and the means to support, so the tendency of the interface between the end surface and support surface to fret is minimized.

18. In a crosshead member for use on a testing machine having a base, the crosshead member being used for loading a test specimen between a first grip member supported on the crosshead member and a second grip member mounted on the base, the specimen being loaded along an axis between the grips, wherein the crosshead is supported relative to the base adjacent its outer edges on load supports and the loading axis is substantially centered between the supports for the crosshead, the improvement comprising:

the crosshead having a plurality of openings through the crosshead symmetrically located relative to the loading axis and between the loading axis and the respective supports, said openings being of size and position so as to alter the lateral stresses in the crosshead and provide a point along the loading axis of substantially zero lateral strain in the crosshead adjacent to and spaced from the grip edge of the crosshead adjacent the first grip;

a counter bore in the grip edge of the crosshead forming an end surface perpendicular to the loading axis and passing through the point of substantially zero lateral strain; and means mechanically supporting the first grip under compression and including a surface mating with the end surface to provide the support interface between the first grip and the crosshead at the end surface.

* * * * *